United States Patent [19]

Hansen et al.

[11] Patent Number: 5,680,858
[45] Date of Patent: Oct. 28, 1997

[54] METHOD AND APPARATUS FOR IN VIVO DETERMINATION OF THE CONCENTRATION IN A BODY FLUID OF METABOLICALLY SIGNIFICANT SUBSTANCES

[75] Inventors: Henrik-Egesborg Hansen, Hellerup; Henrik Ege, Frederiksberg; Thomas Munk Plum, Skodsborg, all of Denmark

[73] Assignee: Novo Nordisk A/S, Bagsvaerd, Denmark

[21] Appl. No.: 448,351

[22] PCT Filed: Dec. 10, 1993

[86] PCT No.: PCT/DK93/00416

§ 371 Date: Jul. 6, 1995

§ 102(e) Date: Jul. 6, 1995

[87] PCT Pub. No.: WO94/13203

PCT Pub. Date: Jun. 23, 1994

[30] Foreign Application Priority Data

Dec. 10, 1992 [DK] Denmark ................. 1485/92

[51] Int. Cl.$^6$ ..................................... A61B 5/05
[52] U.S. Cl. ........................................... 128/635
[58] Field of Search ......................... 128/635, 760, 128/771; 604/289, 290; 204/403

[56] References Cited

U.S. PATENT DOCUMENTS

| | | | |
|---|---|---|---|
| 3,682,159 | 8/1972 | Imredy et al. | 128/635 |
| 3,719,576 | 3/1973 | Macur | 128/635 |
| 3,844,275 | 10/1974 | Elliott | 128/635 |
| 4,637,403 | 1/1987 | Garcia | 128/770 |
| 4,671,288 | 6/1987 | Gough | 128/635 |
| 4,685,463 | 8/1987 | Williams | 128/632 |
| 4,953,552 | 9/1990 | DeMarzo | 128/635 |
| 5,025,798 | 6/1991 | Schindele | 128/771 |
| 5,139,023 | 8/1992 | Stanley | 128/637 |

*Primary Examiner*—Max Hindenburg
*Attorney, Agent, or Firm*—Steve T. Zelson, Esq.; Elias J. Lambiris, Esq.

[57] ABSTRACT

A method for in vivo determination of the concentration in a body fluid of metabolically significant substance comprises storing of a needle with a sensor in a liquid-filled ampoule, brief insertion of the needle into a patient, recording of the output signal from the sensor, withdrawal of the needle, and calculation of the concentration looked for on the basis of the recorded signals. The method is preformed using an apparatus comprising a needle (5) with a sensor (6), an ampoule (1) containing a solution (2) and closed by two membranes (3, 4). The needle (5) is stored with its sensor (6) in the solution. The apparatus further comprises a mechanical unit for driving the needle (5) to protrude from the ampoule for a set moment, and an electronic unit storing the output signal from the sensor (6) and performing calculations on the basis of the stored signal values. The needle with its sensor (6) and the ampoule with the solution (2) are independent disposable parts mounted in a durable part containing the mechanical and electronic parts.

12 Claims, 1 Drawing Sheet

METHOD AND APPARATUS FOR IN VIVO DETERMINATION OF THE CONCENTRATION IN A BODY FLUID OF METABOLICALLY SIGNIFICANT SUBSTANCES

CROSS REFERENCE TO RELATED APPLICATIONS

This application claims priority from PCT/DK93/00414 filed Dec. 10, 1993, which is incorporated herein be reference.

FIELD OF THE INVENTION

The invention relates to a method and a meter for in vivo determination of the concentration in a body fluid of metabolically significant substances.

BACKGROUND OF THE INVENTION

Knowledge of deviations from the accepted normal values in the concentration of metabolically significant substances in the body fluids is of great clinical importance. Especially excursions in the blood glucose concentration must be counteracted without delay by proper adjustments of the diet or the insulin injection regime. Diabetics must therefore have easy access to means for determining the concentration of glucose in their blood or other body fluids. A number of devices for in vitro determination of the concentration of glucose in blood are known.

The devices can be based on optical, chemical or electrochemical properties of glucose, but they all depend on the withdrawal of a small blood sample (about 25 µl). The blood sample can be obtained e.g. by a finger prick or by a cut in the ear lobe. Taking a blood sample is unpleasant and can be painful for many people, because the fingers and the ear lobes are rather sensitive areas. Further, the device used for the analysis will be contaminated with blood which must be wiped off, or the sample receiving part of the device can be disposable, in which case it must be disposed of with care because of the possible contamination with infectious agents.

Consequently, it is the object of the invention to provide a method of analysis and a meter by which a determination of the concentration of metabolically significant substances in the blood is performed using known principles but without the need for taking a blood sample.

SUMMARY OF THE INVENTION

It is known to implant a glucose sensor subcutaneously and to monitor the glucose concentration during a period. Such sensor devices may determine the glucose concentration in the blood or in the interstitial fluid, the latter being only slightly lower than that in blood. No blood sample is taken when using this technique, but it is a disadvantage that the sensor must be implanted for some time before the signal representing the glucose concentration is sufficiently stable. A long (hours) insertion time of the needle is, however, not compatible with the requirements to a personal blood analysing device. A technique with a very short implantation time of the needle can, however, be practised by a method in accordance to the invention and characterized by the steps store a needle with a sensor.

move the needle temporarily so it is inserted into the tissue of the person who's body fluid shall be analysed.

withdraw the needle and calculate the concentration of the significant substance on the basis of the recorded signals.

With this technique the measurement takes place in the subcutaneous tissue of the patient, preferably in the interstitial fluid, making it unnecessary to take a blood sample. The insertion of the needle may cut a few small blood vessels, but especially if the needle is blunt, bleeding and pain associated with the insertion of the needle are usually insignificant. Body areas with low sensitivity, i.e the abdomen or the thigh, can be chosen for the insertion of the needle thus minimizing the pain.

When the needle with the sensor is used more than once it must be disinfected after each use. This is accomplished by storing the needle in an aqueous solution which contains a disinfecting agent e.g. merthiolate. Electrochemical sensors usually require some conditioning time in a suitable buffer before their output signal is stable. It is convenient to let the sterilizing solution serve this purpose. Further, the solution may be used for calibrating the sensor when the solution contains a suitable and constant quantity of the substance which should be determined.

For practical reasons, the time the needle is inserted in the patient should be as short as possible e.g. 1–100 seconds, preferably less than 5 seconds. Some types of sensors may need a longer time for reaching equilibrium, but even when such sensors are used, an insertion time of less than 100 seconds, preferably less than 5 seconds, may be sufficient because the concentration of the substance in question can be calculated from the data recorded when the signal is converging towards the state of equilibrium.

If the sensor is stored in a calibration solution, the signals from the sensor, before and after it has been used, can be compared, and a difference between the signals by more than a set quantity indicates an error, and the measurement should be discarded.

The invention also relates to an apparatus for carrying out the method. Such an apparatus is characterized in that it comprises a needle with a sensor, a vial containing an aqueous solution (which may be suitable for sterilizing, conditioning or calibrating the sensor), the vial being closed by membranes opposite each other, which membranes are leak proof when penetrated by the needle, an electronic unit receiving data from the sensor and having means for storing and processing these data on the basis of set criterions, and means driving the needle to protrude from the vial for a set time and thereafter withdrawing it into the vial.

The sensor may be an electrochemical needle glucose sensor. The shelf life of such a sensor is relatively long, more than one year, when stored in the dry state. In actual use, however, the life time of the sensor is only about a month. It is therefore appropriate that the needle with the sensor and the vial with the aqueous solution are independently disposable, several times usable devices, which are not brought together until some time before the first measurement is made.

The closures of the vial may be rubber membranes which are pierced by the needle. If the membrane is always pierced at the same spot, it will remain leak proof even when it is pierced numerous times. The rubber membrane may be covered by a metal foil as a seal preventing evaporation of water. This is important in order to prolong the shelf life of the vial unit. Especially when the solution in the vial shall be used for calibrating the sensor, only a minute loss of water can be tolerated during the shelf life of the vial. The life time of the vial unit is limited to about one month after it is first used and the membranes and the foils are perforated.

BRIEF DESCRIPTION OF THE DRAWINGS

In the following the invention will be further explained with references to the drawings, wherein.

DETAILED DESCRIPTION OF THE INVENTION

Figure 1:
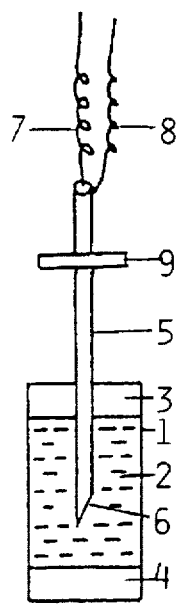
FIG. 1 shows schematically a needle unit and a vial with solution for a measuring apparatus according to the invention.

In FIG. 1 is shown schematically a needle unit with a needle 5 penetrating a membrane 3 which is closing one end of a vial 1 with solution 2. The other end of the vial is closed by a membrane 4. Thereby the pointed end of the needle is positioned in the solution.

The needle for an amperometric glucose sensor is typically made from a stainless steel tubing as used for injection needles. A platinum wire inserted in the bore of the needle, and electrically insulated from the needle, is serving as the anode, while the stainless steel tube can be used as the cathode. The elliptical surface of the obliquely cut and ground end of the needle 6 is coated with a glucose sensitive membrane containing glucose oxidase. When glucose diffuses into the membrane, and a voltage difference (600–700 mV) is applied between the anode and the cathode, an electric current, which in principle is proportional to the glucose concentration in the membrane, will pass from the anode to the cathode. The electrodes are via leads 7 and 8 connected to an electronic unit providing the voltage, measuring the current, and performing the calculations.

The vial 1 containing the solution and being closed by the two rubber membranes 3 and 4 is manufactured as an independent unit. The ends of the vial 1 may further be provided with not shown metal foils covering the rubber membranes and being adhered to the circumferential edge of the vial to provide a vapour tight sealing of the vial, enhancing the shelf life of the vial when filled with an aqueous solution. When the vial is put into service, the metal foils may either be removed before the vial is mounted in the meter, or they may be perforated by the needle.

The needle with the sensor is manufactured as another independent unit. When the needle unit and the vial are put into service, they are placed in a not disposable apparatus comprising a mechanism controlling the insertion and the retraction of the needle and comprising an electronic unit providing the voltage measuring the current and performing the calculations. The needle is provided with a member 9 for engagement with a mechanism in the apparatus, which mechanism governs insertion and retraction of the needle. When the vial unit and the needle unit are mounted in the apparatus, the needle penetrates one of the membranes so that its pointed end with the glucose sensor is positioned in the solution in the vial. Some electrochemical glucose sensors need a relatively long conditioning time, i.e. several hours, before they can be used for measuring. The conditioning may start when the electrode is brought into contact with the solution, and the conditioned state will be maintained as long as the electrode is stored in the solution and the voltage is applied to the anode.

Figure 2:
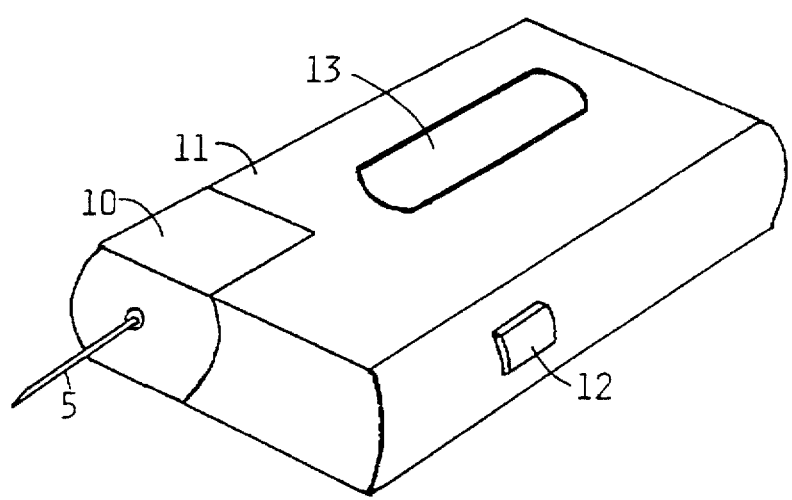
FIG. 2 shows an embodiment of a measuring apparatus.

FIG. 2 shows an embodiment of a measuring apparatus having a housing 11 with a disposable unit 10 comprising a needle unit mounted in a vial as shown in FIG. 1. The housing 11 contains appropriate mechanical and electronic parts for performing a measuring sequence when such a sequence is triggered by operating a button 12. The result of the measurement is displayed on a display 13. When a measuring sequence is triggered, the needle 5 from its position shown in FIG. 1 is moved forward to also penetrate the closure membrane 4 to protrude from the unit 10. This protruding position is maintained for a set time whereafter the needle is retracted to the position with the sensor stored in the aqueous solution in the vial 1.

Figure 3:
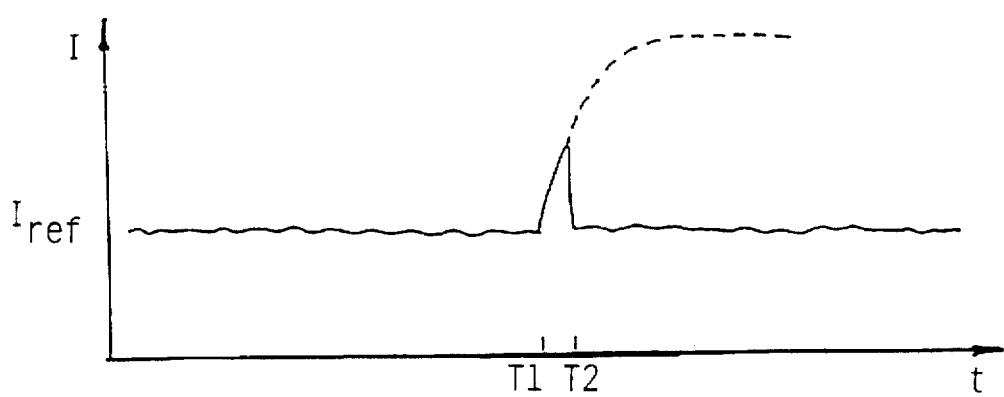
FIG. 3 shows a graph illustrating the current through a glucose oxidase based glucose sensor during an amperometric measuring sequence.

The apparatus with the unit 10 is pressed against the skin in the place where the measurement should be performed, and the apparatus is activated by pressing the trigger button 12. FIG. 3 shows the course of the current during a measurement. Before the apparatus is activated, a reference current is recorded when the needle is located with its sensor membrane inside the vial with the aqueous solution. Thereafter, at the time T1 the needle is shot with its pointed end carrying the sensor through the membrane 4 into the skin of the patient. The needle remains in its inserted position until the time T2, whereafter it is retracted to its position inside the vial 1. At the time T1, when the sensor is passed into the patient, the current will begin to approach the equilibrium value corresponding to the actual glucose content in the blood/interstitial fluid in which the sensor is now situated. This is shown by the dotted graph. Before the equilibrium value is reached, the needle is retracted into the vial 1, and the current will now rapidly return to the reference value, as shown by the fully drawn graph.

As it is seen from the graph, the insertion of the needle is terminated before the equilibrium value of the current is attained, but the initial part of the current graph will contain sufficient information for extrapolating the equilibrium value.

The vial 1 with the aqueous solution and the needle carrying the sensor may be marketed as individual items which may easily be electrically and mechanically coupled to a measuring apparatus. The rubber membranes 3 and 4 should be manufactured from a material which can be pierced multiple times without producing debris and without loosing its leak proof properties. The sealing must be very tight to allow the unit to be stored for say a couple of years before it is put into service. The lifetime of the unit, after at least one of the membrane closures of the vial has been pierced, is estimated to be about one month or about 100 measurements. The lifetime of the disposables is limited by the needle sensor or the aqueous solution deteriorating to a point where their performances are no longer within their specifications.

The apparatus is here described as using a sensor based on enzymatic oxidation of glucose. Another possibility is to use a sensor based on the measurement of some optical characteristics of glucose, or the optical characteristics of a molecule formed by a chemical reaction between glucose and an auxiliary substance. In this case the sensor need not be placed in the needle, but may be located in the not disposable part of the apparatus, and optical signals may be sent from the needle through a light conducting fibre which is coupled to the reusable part of the apparatus when the disposable needle unit is mounted.

We claim:

1. A method for in vivo determination of a body fluid's concentration of at least one metabolically significant substance, the method comprising the steps of:

(a) temporarily inserting a needle for a short duration of time, the needle being stored and having a sensor, into the tissue of a person whose body fluid shall be analyzed;

(b) recording an output signal from the sensor;

(c) withdrawing the needle and (d) calculating the concentration of the metabolically significant substance by extrapolation of the recorded output signal.

2. A method according to claim 1 wherein the needle is inserted for a duration of 1–100 seconds.

3. A method according to claim 1 wherein the needle is inserted for less than 5 seconds.

4. A method according to claim 1 wherein the needle with the sensor is stored in one or more aqueous solutions.

5. A method according to claim 4 wherein at least one aqueous solution is used for sterilizing the sensor.

6. A method according to claim 5 wherein the sterilizing agent is Merthiolate.

7. A method according to claim 4 wherein at least one of the aqueous solutions is used for calibrating the sensor.

8. A method according to claim 7 wherein the output signal from the needle is measured during the storage of the needle in at least one calibrating solution and is compared with the output signal from the sensor when the needle returns to at least one calibrating solution and an error is registered if these signals differ by more than a set amount.

9. A method according to claim 1 wherein the metabolically significant substance is glucose.

10. An apparatus for carrying out the method of claim 1, wherein the apparatus comprises:

(a) a needle being stored and having a sensor at one end and being provided with a member by which the needle can be displaced in its longitudinal direction;

(b) leads connected to the sensor to transmit signals from the sensor to an electronic unit for recording and processing the signals on the basis of set criterions;

(c) a vial containing at least one aqueous solution, the vial being closed by membranes opposite each other at the ends of the vial, which membranes are leak proof when penetrated by the needle, the needle being displaceable perpendicularly to the membranes between a position wherein the needle penetrates one of the membranes so that its end, carrying the sensor, is positioned in the vial between the two membranes and another position wherein the needle penetrates both the membranes so that the needle's end, carrying the sensor, protrudes from one of the membranes.

11. An apparatus according to claim 10 wherein that the sensor is selected from the group consisting of: an electrochemical sensor or optical needle glucose sensor.

12. An apparatus according to claim 10 wherein the needle with the sensor and the vial with the aqueous solution are independently disposable, after being used one or more times.

* * * * *